United States Patent [19]

Green

[11] 4,417,572

[45] Nov. 29, 1983

[54] RESTRAINED PATIENT EXCESSIVE MOVEMENT INDICATING SAFETY DEVICE

[75] Inventor: Frank H. Green, Rushville, Ind.

[73] Assignee: David L. Green, Bratenahl, Ohio; a part interest

[21] Appl. No.: 221,893

[22] Filed: Dec. 31, 1980

[51] Int. Cl.³ .................. A61F 13/00; A61B 5/10
[52] U.S. Cl. ............................. 128/134; 128/782
[58] Field of Search ............... 128/134, 782, 774; 200/DIG. 2, 52 R, 161, 61.93, DIG. 45; 340/573, 575, 668

[56] References Cited

U.S. PATENT DOCUMENTS

| | | | |
|---|---|---|---|
| 1,699,663 | 1/1929 | Hess | 200/61.93 |
| 1,890,679 | 12/1932 | Hallenbeck | |
| 2,036,171 | 3/1936 | Fox | 200/52 R |
| 3,182,338 | 5/1965 | Shirrod | 128/134 |
| 3,236,234 | 2/1966 | Buckley | 128/134 |
| 3,638,647 | 2/1972 | Creelman | 340/668 |
| 3,670,320 | 6/1972 | Palmer | 340/668 |
| 3,924,215 | 12/1975 | Allison | |
| 4,007,733 | 2/1977 | Celeste et al. | 340/573 |
| 4,263,586 | 4/1981 | Nicholas | 340/573 |

FOREIGN PATENT DOCUMENTS 2959 of 1887 United Kingdom .

Primary Examiner—Kyle L. Howell
Assistant Examiner—C. W. Shedd
Attorney, Agent, or Firm—Woodard, Weikart, Emhardt & Naughton

[57] ABSTRACT

Disclosed is an apparatus which includes a moveable, switch-actuating member secured to the strap or belt of a conventional harness restraining a bed patient. The apparatus accommodates the conventional nurse-call push-button switch and the switch is actuated by the moveable member whenever patient movement of abnormal amplitude exerts a sufficient tensional force on the harness. A compression spring is adjustable to determine the force necessary to actuate the switch.

2 Claims, 4 Drawing Figures

4,417,572

RESTRAINED PATIENT EXCESSIVE MOVEMENT INDICATING SAFETY DEVICE

BACKGROUND OF THE INVENTION

In hospitals and nursing homes difficulties have been encountered where patients are restrained in bed and not under direct observation of a nurse or attendant. Such restraint is advisable, particularly during the night, for the patient's protection. Conventionally, a harness or arrangement of straps, such as a Posey belt, is used to permit normal movement of the patient's limbs but prevent leaving the bed; the Posey belt, for example, overlies the trunk of the patient and extends, in figure eight fashion, around the mattress with the two ends of the belt tied together beneath the mattress. Often, a patient so restrained awakes during the night and is confused and disoriented. His initial, determined reaction is to frantically break away from the restraint and get out of bed, the act being attempted, often, with surprising strength because of the patient's confused state of mind. The conventional nurse call-button, accessible at bedside, is ignored by the patient. Whether or not the attempt to leave the bed is successful, because the patient is disoriented and temporarily unaware of the height of the bed, the possibly slippery floor, adjacent night stand or the like, fractures or other injuries to the patient often result.

Patrolling the halls and rooms are intervals is a partial solution to the problem. However, the incidents may occur just after the patient has been observed as asleep and quiet. Tighter or more complete restraint of the patient can cause damaging pressure and circulation restriction and, in general, tighter restraint seems only to trigger a more violent release attempt by the patient during these incidents.

SUMMARY OF THE INVENTION

The concept of the present invention envisages a simple switch actuating structure which is fastened to the free ends of the restraining straps after they are in place on the patient. The moveable, actuating member of the apparatus is thus, in effect, inserted in the restraining strap system so that it is subjected to the tensile force placed on the strap or harness when the patient attempts, in panic, to extricate himself from the straps. A built-in switch, actuated by the moveable member, may be used in the apparatus, or the conventional, hand held, push-button tipped call switch can be incorporated into the apparatus thereby permitting use of the existing call system for alerting the remote nurse station when an incident occurs. A means for adjusting the force required to actuate or trigger the apparatus is provided so that false alarms, resulting from the patients normal body movement in sleep or in reaching for bedside objects, do not occur.

Related objects and advantages of the present invention will be apparent from the following, detailed description.

DESCRIPTION OF THE PREFERRED EMBODIMENT

Figure 3:
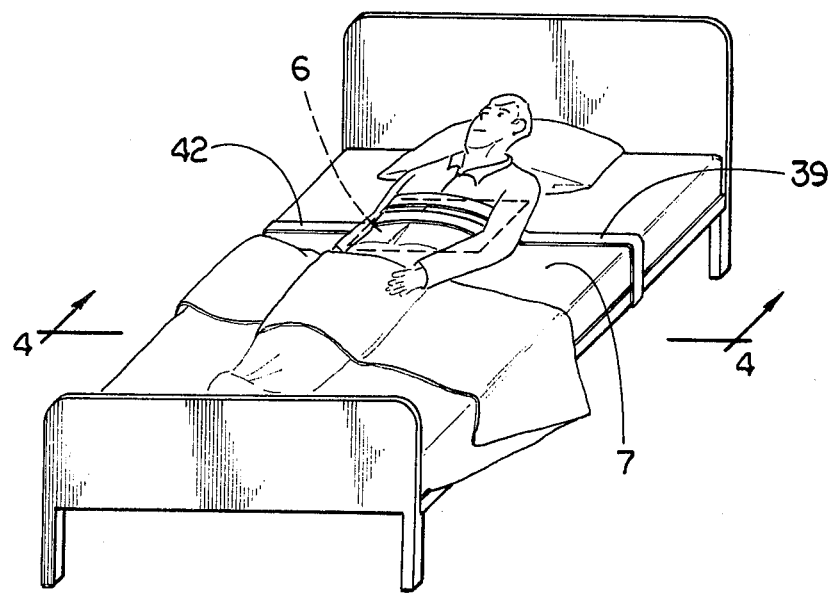
FIG. 3 is a perspective view of a bed with confined patient illustrating the arrangement of a confining belt.

The apparatus of the present invention is used with, or attaches to, a conventional bed-patient restraining harness, such as a Posey belt shown in FIG. 3. The belt is composed of a soft, felt pad 6 (FIG. 3) which normally underlies the patient's body and which has attached to its opposite side margins flexible belts, identified at 39 and 42 in FIG. 3. The ends of the belts may be provided with safety clasps or hooks which may be attached to the bed springs beneath the mattress (identified at 7 in FIG. 3) after the belts have been crossed over the patient's body.

Figure 1:
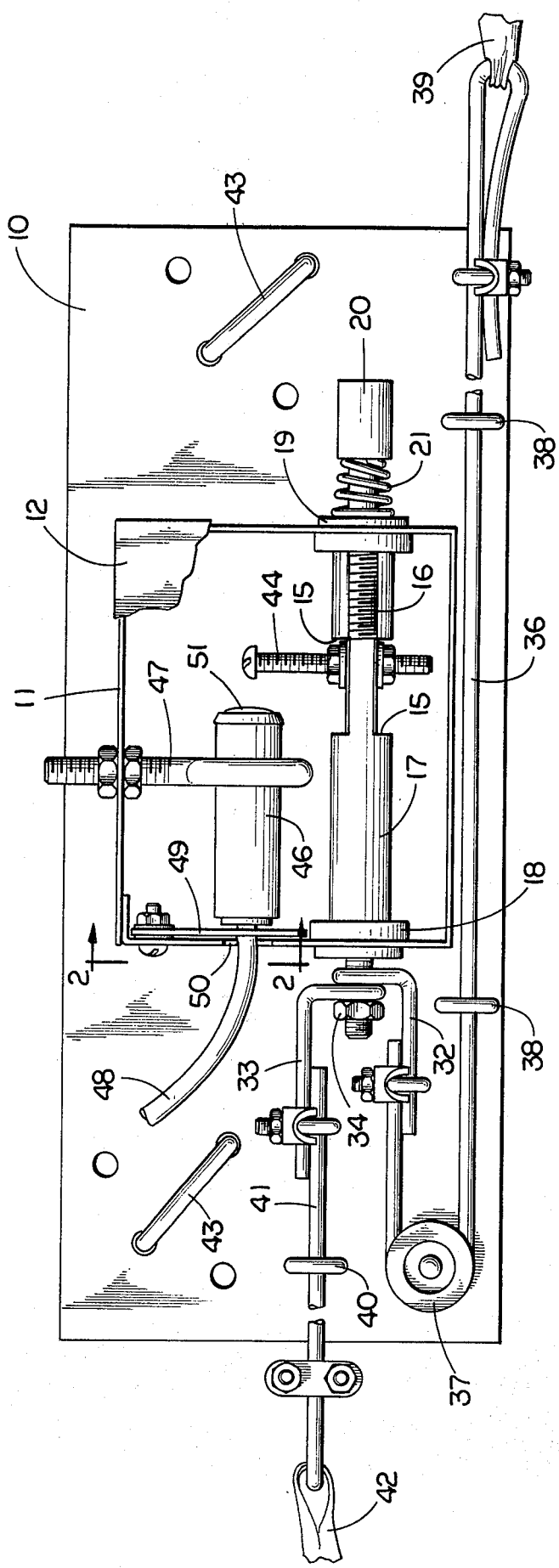
FIG. 1 is a top plan view of apparatus embodying the invention.

Referring to FIG. 1, the apparatus of the present invention includes a base or frame 10 which has mounted thereon a rectangular flanged member or box 11, having a removeable cover fragmentarily shown 12. The box 11 carries opposed bushings 18 and 19 which support a stationary sleeve 17. A moveable member or rod 16 extends through the sleeve and is axially slidable therein.

Threaded on one of the free ends of member 16 is an element 20, and a compression spring 21, encircling the member 16, engages the element 20 and is bottomed on the bushing 19 which is rigidly mounted on member 11. The spring 21 thus urges the member 16 rightwardly, as viewed in FIG. 1, with the adjusted position of element 20 serving to determine the force exerted by the spring on element 20.

The member 16 carries attaching means which includes eyelet members 32 and 33. The members 32 and 33 slide freely on the end portion of member 16 and are retained thereon by a nut 34 threaded on member 16. The member 32 has attached to it a length of flexible cord or cable 36 which extends around a direction reversing idler pulley 37, through guiding eyelets 38, and extends beyond the base 10 for attachment to one end of the strap (shown fragmentarily at 39 in FIG. 1) of the conventional bed patient restraining harness. Eyelet member 33 has attached to it a flexible cable length 41 which extends beyond the base 10 and is tied to the other end strap 42 of the patient restraining harness.

Figure 2:
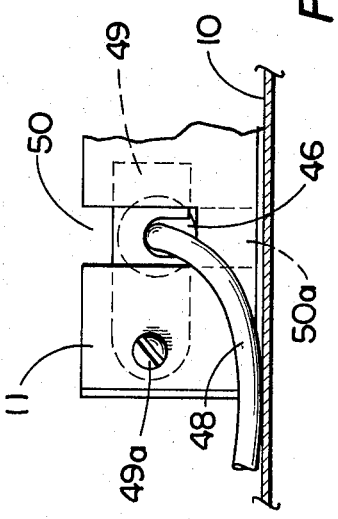
FIG. 2 is a fragmentary, side view taken generally along the line 2—2 of FIG. 1.

U-bolts 43 extend through the base and are adapted for attachment to the bedsprings so that the base can be mounted between the mattress and spring components of the bed as will subsequently be described with reference to FIG. 4. The rod 16, generally intermediate its length, carries a pin or abutment 44 which extends through opposed longitudinal slots 15 in the sleeve 17. The abutment is adapted to engage the push-button tip 51 of a conventional, cylindrically-shaped, hand-held call switch 46. The switch is inserted freely into the eyelet member 47, extending from the flange 11, with its cable 48 extending through a slot 50 in the flange 11. A pivotally mounted member 49, when in the substantially horizontal position shown in FIG. 2, locks the cable in the slot 50 and backs the rear face of switch 46. As will be evident from FIG. 2, the tongue 50a, struck from the member 11 to form slot 50, is bent downwardly so that its free end engages the base 10, the tongue thus serving as a supporting member for the rear portion of switch 46 holding it substantially aligned with eyelet member 47. The member 49 may be moved counterclockwise (as viewed in FIG. 2) about its pivot 49a to permit removal or replacement of switch 46 in the apparatus.

It will be understood that, as is conventional, the jack (not shown) at the end of cable 48 is plugged into a wall receptacle (not shown) and the condition of switch 46 is signalled on a panel at a remote nurses' station. Conventionally, the jack has two, parallel-connected, switchtipped cables extending from it and one may be utilized for mounting in the apparatus of the present invention and the other to provide normal, hand-held call switch service. The abutment 44 is adapted to engage and depress the push-button 51 on the switch 46 when member 16 has been moved leftwardly (as viewed in FIG. 1) a predetermined distance against the restoring force exerted by spring 21. It will be understood that a built-in switch might replace conventional call switch 46, however, the arrangement shown permits utilization of the conventional hand-held switch 46, standard equipment at such facilities as hospitals and nursing homes.

Figure 4:
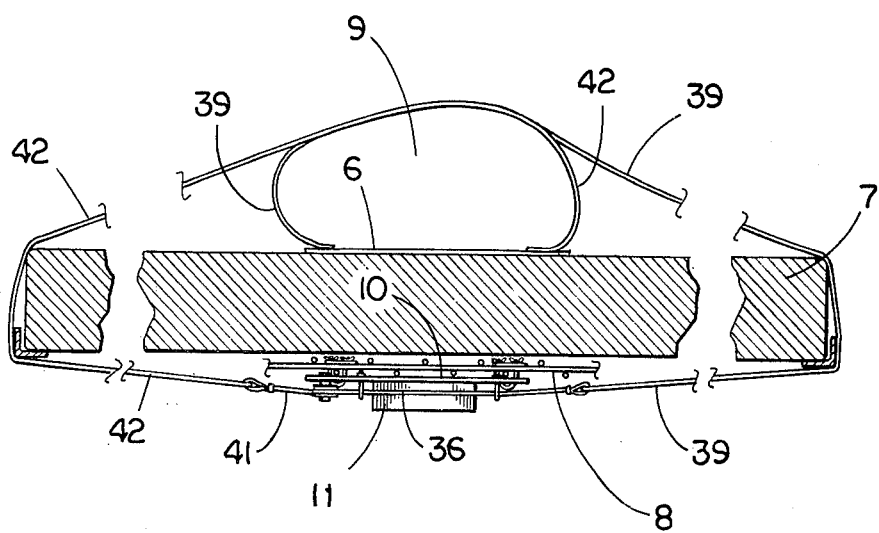
FIG. 4 is a fragmentary sectional view taken generally along the line 4—4 of FIG. 3 and illustrating the location of the structure shown in FIG. 1.

The incorporation of the apparatus of the present invention into the patient restraining system is illustrated in FIG. 4. The frame 10 may be placed under the mattress and bed spring component (shown fragmentarily at 8 in FIG. 4) and straps 39 and 42 are secured to cables 36 and 41, respectively. It will be understood that the space identified at 9 in FIG. 4 is occupied by the trunk of the restrained patient.

In operation, with the apparatus of the present invention in place beneath the mattress of a patient restrained by a conventional strap arrangement, such as a Posey belt, the member 20 is positioned so that normal body movement of the patient is insufficient to actuate switch 46. Gross body movements of the patient, such as occur when the patient attempts to leave the bed will cause sufficient movement of member 16 to actuate switch 46, signalling the remote nurses' station.

It should be noted that the incorporation of the apparatus of the restraining system shown in FIGS. 3 and 4 provides complete monitoring of the patient's movements. Any gross movement of the patient over a 180 degree range in the vertical plane or over the complete 360 degree range in the horizontal plane (the plane of the mattress' upper surface) will cause actuation of switch 46 and, consequently, an alarm signal. For example, electrical wires 61 and 62 extend through cable 48 and are operably connected to switch 46 and to a suitable source of electrical energy 63 and alarm 64. Thus, gross movement of the patient causing actuation of switch 46 will complete the circuit between wires 61 and 62 thereby actuating alarm 64 located at the nurse station. In lieu of an audio alarm 64, a visual alarm may be utilized. The patient cannot escape over the foot, head or sides of the bed and cannot raise himself directly above the bed to any substantial degree without tripping the alarm signal.

While the invention has been illustrated and described in detail in the drawings and foregoing description, this is to be considered as illustrative and not restrictive in character, it being understood that only the preferred embodiment has been shown and described and that all changes and modifications that come within the spirit of the invention are intended to be protected.

What is claimed is:

1. An apparatus for detecting body movements of abnormal amplitude by patients restrained in bed with conventional strap or harness members, said apparatus comprising a base, a moveable member mounted for movement on the base, a push-button actuated switch means operable to activate an alarm when its push-button is depressed, said means including a switch being mounted on said base adjacent said moveable member with the axis of motion of its push-button parallel to the axis of motion of said moveable member, an abutment carried by said moveable member intermediate its ends and positioned to engage and depress said push-button upon a predetermined movement of said moveable member, resilient means biasing said moveable member in a direction spacing said abutment from the push-button, and attaching means for joining said moveable member to said conventional strap or harness members to thereby exert a motion producing force on said moveable member which is resisted by said resilient means and which motion is a direct function of the tensional force applied to the strap or harness members by the movement of the patient; said push-button actuated switch being a conventional, hand-held push-button, call switch, said moveable member having a threaded portion, and a correspondingly threaded element received upon said threaded portion, said resilient means being a compression spring that encircles said threaded portion and is bottomed on a portion of said base and biases said threaded element from said base portion, the position of said element on said threaded portion thus determining the biasing force exerted by said spring on said moveable member; said switch having a cable extending therefrom which is removably mounted on said base, said base further including a sidewall having a cable receiving slot, said sidewall further including a moveably mounted gate, adjacent said slot, that lockingly engages said cable.

2. The apparatus of claim 1 wherein:
said slot is formed by folding over a portion of said sidewall and thereby forming a tongue-shaped portion extending toward said base for supportingly receiving said switch.

* * * * *